United States Patent [19]

Seid

[11] Patent Number: 5,254,133
[45] Date of Patent: Oct. 19, 1993

[54] SURGICAL IMPLANTATION DEVICE AND RELATED METHOD OF USE

[76] Inventor: Arnold S. Seid, 427 16th St., Santa Monica, Calif. 90402

[21] Appl. No.: 690,774

[22] Filed: Apr. 24, 1991

[51] Int. Cl.$^5$ ............................................. A61B 17/04
[52] U.S. Cl. .................................. 606/215; 606/151; 606/213; 128/899
[58] Field of Search ............... 606/213, 215, 232, 151; 128/899

[56] References Cited

U.S. PATENT DOCUMENTS

| | | | |
|---|---|---|---|
| 3,707,150 | 12/1972 | Montgomery et al. | 606/151 |
| 3,874,388 | 4/1975 | King et al. | 606/213 |
| 4,007,743 | 2/1977 | Blake | 606/213 |
| 4,031,569 | 6/1977 | Jacob | 128/899 |
| 4,769,038 | 9/1988 | Bendavid et al. | |
| 4,854,316 | 8/1989 | Davis | 128/898 |
| 4,917,089 | 4/1990 | Sideris | 606/215 |
| 5,021,059 | 6/1991 | Kensey et al. | 606/213 |
| 5,108,420 | 4/1992 | Marks | 606/213 |
| 5,116,357 | 5/1992 | Eberbach | 606/151 |

FOREIGN PATENT DOCUMENTS

WO90/14796 12/1990 World Int. Prop. O. .......... 606/213

Primary Examiner—Stephen C. Pellegrino
Assistant Examiner—Jeffrey A. Schmidt
Attorney, Agent, or Firm—Pretty, Schroeder, Brueggemann & Clark

[57] ABSTRACT

A surgical implantation device to be placed within a patient's body and seal a hernial rupture includes either a single planar member attached to a locating segment or a first planar member and second planar member, large enough to cover the opening in the abdominal fascia, that are placed on opposite sides of the fascia. In the case of a single planar member, the locating member is placed in the fascia opening and the planar member is placed interiorly of the transversalis fascia. In the case of two planar members, the first and second planar members are connected by a locating member that passes through the fascia opening. The surgical implantation device can be folded upon itself and compressed to fit with a surgical tube and inserted into the patient to the hernial site. Once the surgical tube is at the site, the surgical implantation device is forced from the tube and automatically expands so the planar members assume their flat shape and the locating member assumes its elongated shape.

13 Claims, 4 Drawing Sheets fig. 1.

SURGICAL IMPLANTATION DEVICE AND RELATED METHOD OF USE

BACKGROUND OF THE INVENTION

1. Field of the Invention

This invention relates generally to surgical implantation devices and, more particularly, to surgical implantation devices that are used to repair openings in the walls of body cavities.

2. Description of the Related Art

The present invention can be used in treating an inguinal hernia, for example. Inguinal hernia is a painful condition in which the wall of the abdominal cavity ruptures and a portion of the peritoneum protrudes through the opening in the abdominal wall. The portion of the peritoneum protruding through the abdominal wall must be tied off and pushed back into place and the opening in the wall must be sealed to prevent further injury and infection. These tasks must be accomplished using surgical techniques.

Figure 1:
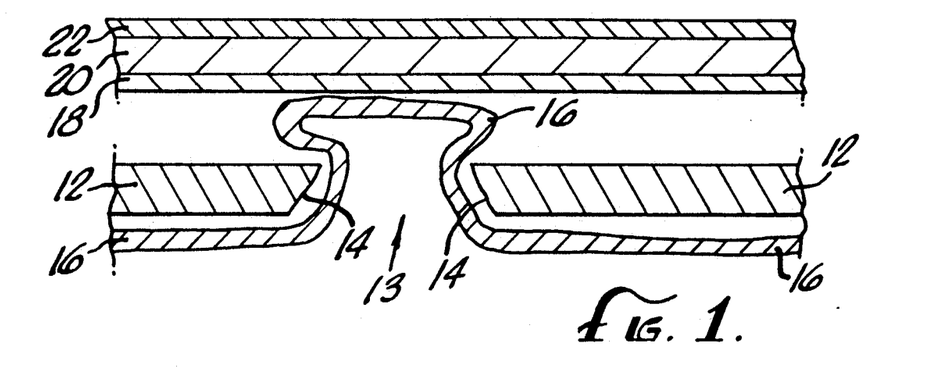
FIG. 1 is a cross-sectional view of tissue layers in a patient showing a hernia condition.

FIG. 1 is a cross-sectional view of a patient with a hernia condition in which the transversalis fascia 12, or abdominal wall, has a ruptured opening 13 with angled edges 14 in the wall defining a frusto-conical circumference. The peritoneum 16 is a membrane that lines the abdominal cavity and acts as a cover for the internal organs, including the intestine (not shown). When the rupture is large enough, typically approximately one centimeter in diameter, the peritoneum and the internal organs behind it can suddenly protrude outwardly past the rupture into the space behind the external oblique muscle 18. This can strain the muscle and press it against the overlaying subcutaneous fat 20 and the skin 22.

One surgical technique commonly used to treat the hernia and seal the rupture is to make an incision in the skin 22 followed by dissection through the subcutaneous fat 20 and external oblique muscle 18 to reach the opening in the transversalis fascia 12. Once exposed, the portion of peritoneum 16 extending through the rupture can be tied off and pushed back to the proper side of the fascia. The opening in the fascia can then be repaired by pulling the opening's angled edges 14 together and keeping them closed by using sutures or surgical staples. This surgical technique can lead to great post-operative discomfort because of the need to cut through many layers of tissue. The large incision requires careful post-operative care to prevent infection from the outside and produces great discomfort while the wound heals. Pulling the opening in the fascia closed also creates a tension on the fascia, which results in additional discomfort. Thus, the incision and the pulling together of the fascia both create difficulties in post-operative recovery.

Figure 2:
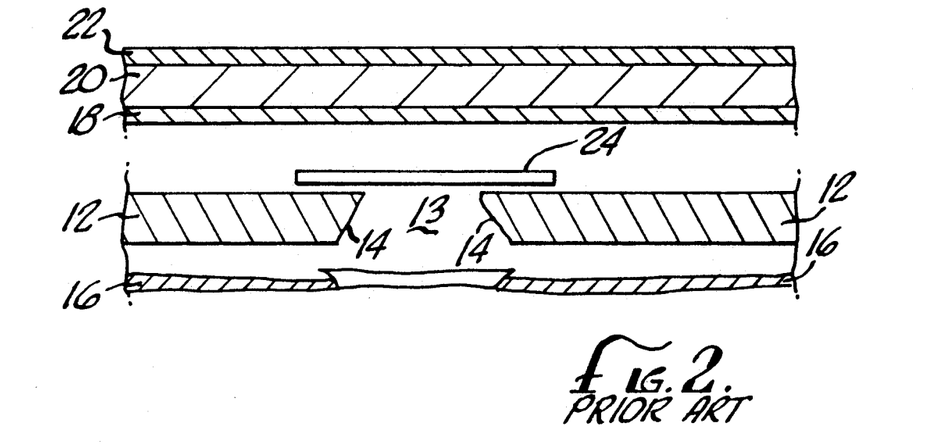
FIG. 2 is a cross-sectional view of the layers of tissue in a hernia patient with a conventional surgical implantation device.

Another surgical technique commonly used to repair hernias uses a biocompatible prosthetic patch constructed from, for example, polypropylene. The patch is positioned on one side of the fascia, bridging the opening 13. Alternatively, with relatively small openings, the patch is rolled up and inserted lengthwise into the opening, plugging it. In either case, with the passage of time body tissue will grow around and onto the patch and hold it in place. FIG. 2 is a cross-sectional view showing a prosthetic patch 24 placed on top of the fascia 12 covering the opening 13 in accordance with this technique. Unfortunately, the prosthetic patch can move about in relation to the opening before tissue has grown onto it. Such movement produces a less than optimal result and possibly a failure of the seal. In addition, the large incision in the skin 22, with the concomitant discomfort and post-operative difficulties, is still a problem.

More recently, less invasive surgical procedures have been used in conjunction with a laparoscope. A typical laparoscope includes a one-centimeter diameter surgical tube that can be inserted through the patient's skin and through the peritoneum 16 into the peritoneal cavity, toward the center of the abdomen interiorly of the peritoneum. Thus, the surgical tube is approximately of the same diameter as the hernia opening 13 and leaves a relatively small wound. The surgeon views an optical image through the surgical tube and can see the progress of the tube's end as it makes its way in the peritoneal cavity toward the site of the opening. The peritoneum can either be left intact while the tube's end is moved to the opening 13 or the peritoneum can be cut open to extend the tube's end out of the peritoneal cavity to the opening.

At the transversalis fascia opening 13, a prosthetic patch inserted down the length of the surgical tube can be forced out of the tube and moved into its desired position. Post-operative problems are decreased by this procedure because of the smaller external wound left by the surgical tube. The patch, however, still can shift before tissue has grown onto it. The prosthetic patch also can be sutured to the transversalis fascia or peritoneum, to minimize movement. Unfortunately, it can be very difficult to attach the prosthetic patch with sutures using the laparoscope because of difficulties in viewing and in maneuvering through the laparoscope.

From the discussion above, it should be apparent that there is a need for a surgical implantation device and technique for using it that minimize patient discomfort and provide an easier post-operative recovery, that minimize shifting of the device before tissue has grown into place, and that eliminate the need for surgical dissection. The present invention satisfies this need.

SUMMARY OF THE INVENTION

The invention provides a surgical implantation device that can be used with a laparoscope to minimize the external wound necessary for placement of the implantation device and that can be compressed into an implanting condition for placement at the opening in the transversalis fascia using the laparoscope and then can be expanded into a deployed condition to securely seal the opening. In the implanting condition, the surgical implantation device is compressed to a size small enough to fit within the hollow surgical tube of the laparoscope. Once the surgical tube is placed in its proper position at the fascia opening, the surgical implantation device is pushed out the end of the tube and is expanded into the deployed condition, effectively bridging the opening in the transversalis fascia. The surgical implantation device is effectively immobilized in place when in the deployed condition, thereby preventing its movement out of the fascia opening while tissue grows around it. The peritoneum can either be left intact and pushed through the fascia opening by the surgical tube and held in place by the surgical implant device, or the peritoneum can be pierced and the surgical tube and device can be positioned directly in the fascia opening.

In one aspect of the invention, the surgical implantation device comprises an expandable planar member attached to a biocompatible locating plug member. The planar member and locating plug member are compressible such that, in the implanting condition, both members can fit within the surgical tube of the laparoscope, the locating plug being inserted first. The end of the surgical tube is first placed at the opening in the transversalis fascia, with the peritoneum either left intact or pierced. The locating plug is then pushed out of the surgical tube such that it fills the opening in the transversalis fascia. The planar member is then pushed out of the tube, whereupon it automatically expands and assumes a planar orientation adjacent the inner surface of the transversalis fascia. The planar member is held in place by the locating plug and by pressure from the intestine and other tissues in the peritoneal cavity. Thus, the surgical implantation device is immobilized in position while the planar member automatically assumes an expanded condition in which it bridges the opening in the transversalis fascia.

In another aspect of the invention, the surgical implantation device includes two biocompatible planar members, or patches, that are placed on either side of the transversalis fascia at the opening and also includes a biocompatible locating plug member that passes through the opening and connects the two planar members together. The members are compressible such that, in the implanting condition, all three members can fit within the surgical tube of the laparoscope. The end of the surgical tube is placed through the opening in the fascia, with the peritoneum either left intact or pierced, and the device is left compressed in the tube. The first planar member is then pushed out the end of the laparoscope tube, whereupon it is automatically expanded into its planar deployed condition in front of the fascia. The elongated biocompatible locating member is next left in place as the tube is withdrawn through the opening so that it occupies the opening in the fascia and extends between the front surface and back surface of the fascia. Next, the last biocompatible planar member is pushed out the end of the tube, automatically expanding into its planar deployed condition adjacent the back surface of the fascia. Each planar member is therefore immobilized in position by its connection to the opposite planar member. If the peritoneum was pierced, it is then sutured or stapled together.

The planar members and connecting length of locating material can be formed from a wide variety of biocompatible materials. These materials include fabrics such as "MARLEX"-polypropylene, "MERSILENE"-"DACRON", and "GORE-TEX"-polytetraflourethelene. For example, the planar members can comprise fabric patches made from these materials. Alternatively, the planar members can comprise co-planar spoked segments that emanate radially from a hub. In either case, the members can be automatically expanded into their deployed condition by constructing them with a variety of resilient materials that have memory. The resilient materials can be embedded in or attached to the fabric patches and include nylon, polypropylene, or silastic materials, for example. The resilient materials can be embedded or attached to the fabric patches in multiple strands emanating radially or concentrically from the center of the patch or in a single strand along the periphery of the patch. Alternatively, the patches can be made entirely from the resilient materials.

The surgical implantation device can be implanted as a single piece or can be pushed down the laparoscope tube as individual component parts and assembled at the hernia site. A suture attached to the first planar member can act as a guide string for the remaining members. Additionally, a staple technique can be used to attach the parts together before insertion. The component parts, if inserted individually, can be attached together at the opening by using a hook-and-loop fastener arrangement, such as "VELCRO", or by using sutures.

Other features and advantages of the present invention should be apparent from the following description of the preferred embodiments, taken in conjunction with the accompanying drawings, which illustrate, by way of example, the principles of the invention.

DESCRIPTION OF THE PREFERRED EMBODIMENTS

Figure 3:
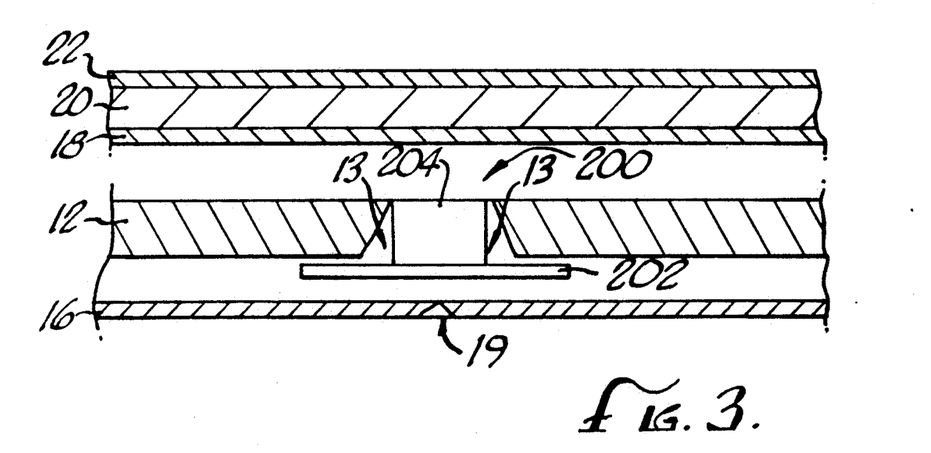
FIG. 3 is a cross-sectional view of the layers of tissue in a hernia patient with a surgical implantation device constructed in accordance with the present invention in its deployed condition.

FIG. 3 shows a fully deployed surgical implantation device 200 in accordance with the present invention, which provides an effective seal against a rupture 13 in the transversalis fascia 12 of a patient and which is effectively immobilized in place while the patient's tissue grows onto it. The implantation device can be inserted into the peritoneal cavity past the peritoneum 16 using a laparoscope, which eliminates the need for making a long incision and dissecting through the skin 22, subcutaneous fat 20, and transversal oblique muscle 18. Instead, the device can be pushed out the end of a laparoscope, as described in further detail below, either by first piercing the peritoneum 16 or by leaving the peritoneum intact. FIG. 3 illustrates the device in place after the peritoneum has been pierced, the device deployed, and the peritoneum sutured at 19.

The implantation device 200 includes a planar member 202 attached to a biocompatible locating plug member 204. Both members are compressible such that they can fit within the surgical tube of a laparoscope, which has a diameter of approximately one centimeter. A typical transversalis fascia rupture 13 has a diameter of approximately one centimeter, therefore the only external wound necessary to insert the surgical implantation device 200 is a one centimeter diameter hole left by the surgical tube. Thus, the surgical implantation device 200 in accordance with the present invention minimizes the amount of trauma to the patient due to the surgical procedure itself. Because there is no dissection through layers of body tissues and no stretching of the transversalis fascia 12, the post-operative discomfort of the patient is minimized. Moreover, the implantation device is held in place by the fit of the plug member 204 in the opening 13 and by the force of the patient's intestine and other internal organs in the peritoneal cavity pressing against the planar member 202. Thus, the implantation device is securely fixed in place while the patient heals.

The planar member 202 can be provided in a variety of structures. For example, the planar member can comprise a biocompatible fabric patch that is provided with resilient expandable elements. Alternatively, the planar member can comprise a plurality of resilient segments that radiate outwardly from the center of the biocompatible locating plug 204. Finally, the planar member and plug can be a single integrated structure or can be separately attached together either prior to insertion in the laparoscope's surgical tube or in situ. These alternative constructions are described further below in conjunction with descriptions of other embodiments of the present invention.

Figure 4:
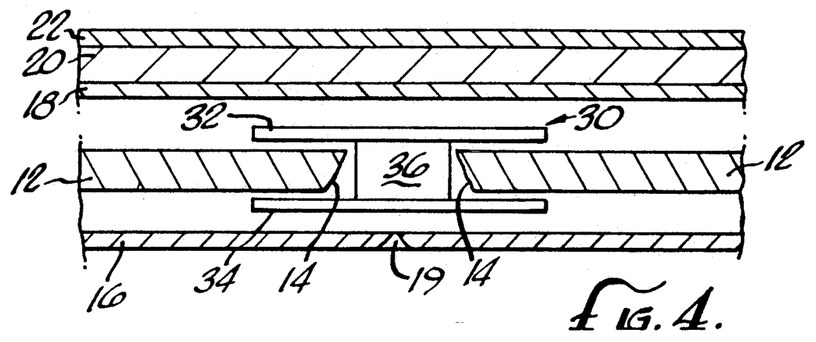
FIG. 4 is a cross-sectional view of the layers of tissue in a hernia patient with a surgical implantation device, constructed in accordance with the present invention, in its deployed condition after the peritoneum has been cut and the device has been placed on the outside of the peritoneal cavity.
Figure 5:
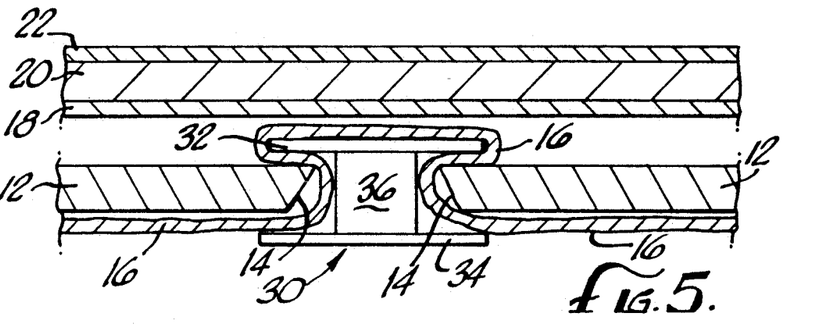
FIG. 5 is a cross-sectional view of the layers of tissue in a hernia patient with the surgical implant device illustrated in FIG. 4 in its deployed condition, using a procedure that leaves the peritoneum intact.

FIG. 4 shows an alternative embodiment of a fully deployed surgical implantation device 30 in accordance with the present invention. This embodiment also provides an effective seal against a rupture in the transversalis fascia 12 of a patient and is effectively immobilized in place while the patient's tissue grows onto it. As with the FIG. 3 embodiment, the implantation device 30 can be inserted into the peritoneal cavity past the peritoneum 16 using a laparoscope, which eliminates the need for making a long incision and dissecting through the skin 22, subcutaneous fat 20, and transversal oblique muscle 18. Instead, the device can be pushed out the end of the laparoscope's surgical tube (shown in FIGS. 6-8) to the site of the rupture by either first piercing the peritoneum 16 (FIG. 4) or by leaving the peritoneum intact (FIG. 5). The surgical tube has a diameter of approximately one centimeter, which is about the size of a typical fascia rupture 13, and therefore the only external wound necessary is a one centimeter diameter hole left by the surgical tube. Thus, a surgical implantation device in accordance with the present invention minimizes the amount of trauma to the patient due to the surgical procedure itself, improves the fixation of the implantation device in the fascia opening, and minimizes the post-operative discomfort the patient will experience because there is no dissection through layers of body tissues, no stretching of the fascia, and minimal movement before tissue has grown around the implantation device itself.

The implantation device illustrated in FIG. 4 includes two planar patches located on opposite sides of the transversalis fascia 12 and connected by a locating segment that substantially fills the transversalis fascia opening 13. In a preferred embodiment illustrated in FIG. 4 and FIG. 5, the implantation device 30 includes a first biocompatible circular fabric patch 32 located on one side of the opening above the fascia 12, a second biocompatible circular fabric patch 34 located on the opposite side of the fascia, and an elongated, biocompatible locating segment 36 linking the first and second fabric patches together and extending between the opening's angled sides 14. The patches and locating segment can be a single integrated structure or the patches can be attached to the locating segment, as described in further detail below.

Each of the fabric patches 32 and 34 is circular, so as to be more easily compressed into an implanting condition and automatically expanded into a deployed condition. Alternatively, one or both of the patches can be non-circular, particularly where the fascia opening is located laterally, as described further below. The fabric can be any biocompatible material, the most popular materials for this application being "MARLEX"-polypropylene, "MERSILENE"-"DACRON", and "GORE-TEX"-polytetraflourethelene. The fabric patches are automatically expanded into their deployed condition when they are pushed from the end of the surgical tube. The automatic deployment can be achieved with a wide variety of materials. The only requirement for automatic deployment is that the materials have memory, i.e., can be compressed from an expanded, at-rest condition to a compressed condition, and then automatically regain their expanded shape when the compression is released. Suitable materials include nylon, polypropylene, or silastic materials or resilient stainless steel strips or springs. These materials can be formed in the shape of flat ribbons, circular threads, or coiled springs and can be embedded or attached to the fabric patches either radially, circularly, or circumferentially. Alternatively, the entire implantation device can be constructed of these materials.

Figure 6:
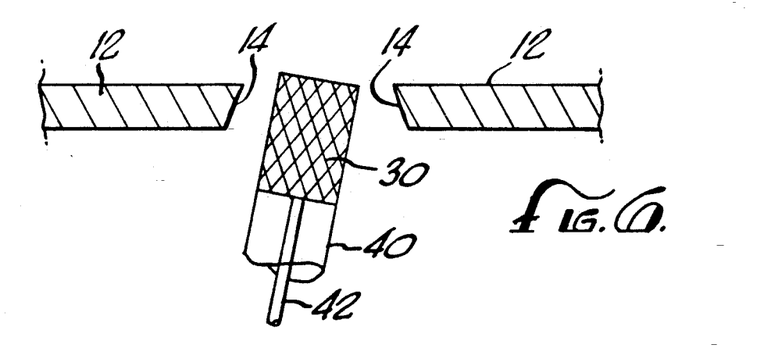
FIG. 6 is a cross-sectional view of the surgical implantation device shown in FIG. 4 in an implanting condition fully within the laparoscopic surgical tube.
Figure 7:
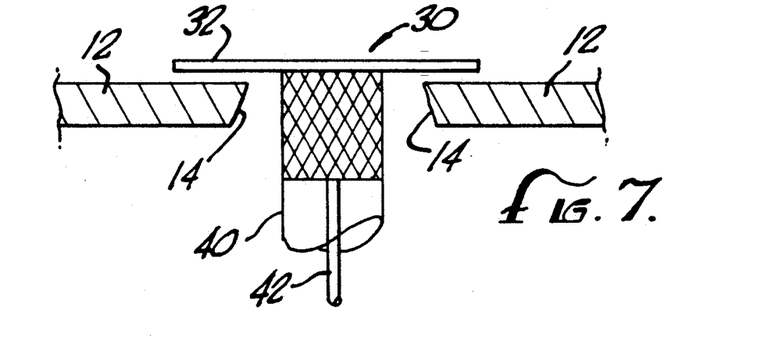
FIG. 7 is a cross-sectional view of the FIG. 6 surgical implantation device in a partially deployed condition.
Figure 8:
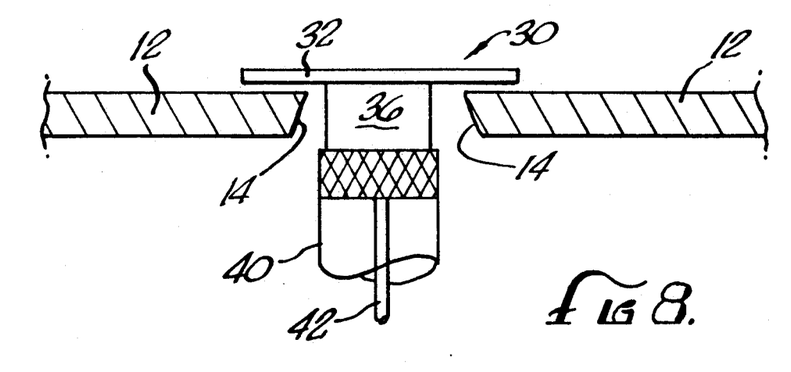
FIG. 8 is a cross-sectional view of the FIG. 6 surgical implantation device shown with the first fabric patch and connecting material pushed out from the end of the laparoscopic tube.

Because the surgical implantation device 30 in accordance with the present invention can be compressed and expanded, it can advantageously be positioned within the patient using a laparoscope, as shown in FIGS. 6-8. Surrounding layers of tissue have been omitted for the sake of clarity. Although the views of FIGS. 6-8 are shown without the peritoneum, thereby indicating that the peritoneum has been pierced and the device implanted outside of the peritoneal cavity as illustrated in FIG. 4, it is to be understood that the device works equally well with a procedure that leaves the peritoneum intact as illustrated in FIG. 5.

In FIGS. 6-8, the surgical implantation device 30 is first compressed and placed within the surgical tube 40 of the laparoscope. The compressed implantation device is represented in FIGS. 6-8 by the cross-hatched area in the surgical tube. As known to those skilled in the art, the surgical tube is pushed through the patient's outer skin 22 and through all intermediate layers such as the transversalis fascia 12 and the peritoneum 16 until it reaches the peritoneal cavity. The surgical tube is then advanced within the peritoneal cavity up to the site of the fascia opening 13, or hernia. The peritoneum 16 is then pierced and the end of the surgical tube 40 is placed at the opening 13. A rigid pushing tool 42 is then inserted down the surgical tube until it is in a position to push the surgical implantation device 30 out of the surgical tube.

When the surgical tube 40 is in a location relative to the opening 13 in the transversalis fascia 12 as illustrated in FIG. 6 and the surgical implantation device 30 is pushed out of the surgical tube, the first fabric patch 32 of the surgical implantation device automatically expands and deploys as it is forced from the surgical tube. When the first patch deploys, it assumes a generally circular, planar configuration extending parallel to the fascia 12 so as to bridge the angled sides 14 of the fascia opening as illustrated in FIG. 7.

The surgeon then continues to deploy the surgical implantation device 30 at the opening 13 in the transversalis fascia 12 by withdrawing the surgical tube 40 from its position in the fascia opening. As illustrated in FIG. 8, the locating member 36 is the next portion of the device to be pushed from the surgical tube. The locating member has a diameter of approximately one centimeter, approximately equal to the diameter of the typical fascia opening. The locating member 36 can be solid and have a diameter as large as the surgical tube. Alternatively, the locating member can be resilient and have a diameter greater than that of the surgical tube. In such a case, the locating member must be constructed from a flexible material such that the locating member can be compressed into a size small enough to fit within the surgical tube. As illustrated in FIG. 8, the deployed locating member has a diameter approximately equal to that of the opening 13 in the fascia. Thus, when the locating member is deployed, it effectively prevents lateral movement of the first fabric patch 32 relative to the fascia and locates the device in the proper position.

When the second fabric patch 34 of the surgical implantation device 30 is pushed out from the surgical tube 40, the patch automatically expands and deploys into a generally planar patch, as shown in FIG. 4 and FIG. 5. As can be seen from FIG. 4 and FIG. 5, the two planar patches 32 and 34 are held in place relative to the opening 13 in the fascia 12 by the locating member 36. The patches are effectively immobilized relative to the opening in the fascia because the locating member has a diameter approximately equal to that of a typical opening in the fascia and has a length only slightly greater than the thickness of the typical fascia.

Figure 9:
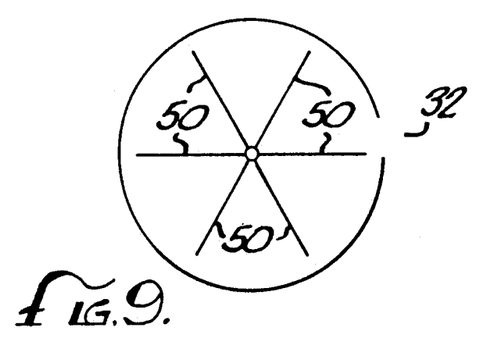
FIG. 9 is a top plan view of the FIG. 4 surgical implantation device in the deployed condition.

A wide variety of materials can be used for the various elements of the surgical implantation device, as noted above. The resiliency, or memory, of the surgical implantation device likewise can be provided in a variety of ways. For example, nylon or spring steel segments can be attached or sewn into the patches. FIG. 9 is a plan view of an expanded surgical implantation device with the first portion 32 of the device constructed from a biocompatible fabric. A plurality of nylon or spring steel memory segments 50 are shown attached to the fabric in straight lengths emanating radially from the center of the patch. The memory segments are flexible enough to be folded upon themselves so as to allow the device to fit within the surgical tube 40 of a laparoscope. Once inside the surgical tube, the device remains in its compressed condition because of the tube walls. Once the surgical implantation device has been pushed from the surgical tube, the memory segments 50 resume their earlier straight shape, unfolding themselves flat and giving the fabric patch 32 a planar shape.

Figure 10:
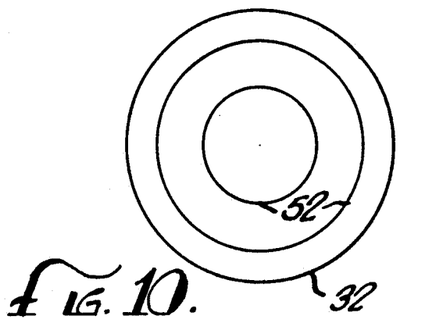
FIG. 10 is a top plan view of an alternate embodiment of a surgical implantation device constructed in accordance with the present invention.

FIG. 10 illustrates a first portion 32 of a surgical implantation device similar to that shown in FIG. 9, this time having its shape restored by a plurality of flexible memory segments 52 attached to the fabric patch in concentric circles emanating from the center of the first portion 32

Figure 11:
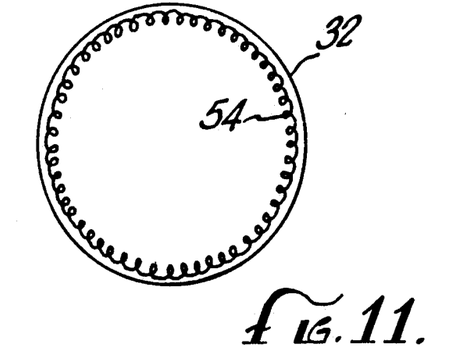
FIG. 11 is a top plan view of yet another embodiment of a surgical implantation device constructed in accordance with the present invention.

Yet another possible configuration for the implant is illustrated in FIG. 11, wherein a first implant portion 32 constructed from a biocompatible fabric patch is provided with an elongated spring steel coil 54 that is attached to the fabric patch along the patch's circumference. When unstrained or unfolded, the coil tends to lay flat, giving the fabric patch a planar configuration. The coil also has enough resilience to be compressed so as to fit within the laparoscope and then automatically expand when pushed from the laparoscope tube.

Figure 12:
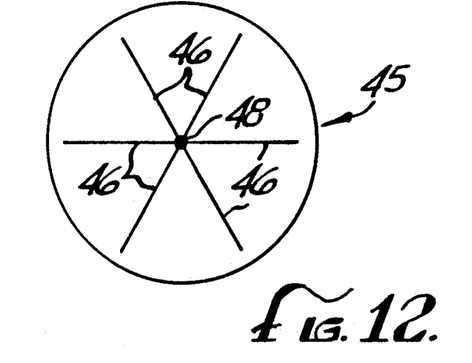
FIG. 12 is a top plan view of another alternative embodiment of a surgical implantation device in accordance with the present invention.

It is not necessary for the planar patches to comprise pieces of fabric. FIG. 12 shows a plan view of an alternative embodiment in which the planar patch 45 comprises a plurality of spoke segments 46 emanating from a central hub 48. The spoke segments are resilient enough to be compressed and fit into the surgical tube 40. When the planar patch 45 is pushed out of the tube, the spokes regain their radially-directed shape as shown in FIG. 12. In side view, the spoke planar member 45 appears as the planar patches shown in FIGS. 3-8. While the spokes 46 do comprise separate segments, they are coplanar and therefore provide a structure that is located on one side of the transversalis fascia 12 and that provides a planar structure to bridge the fascia opening 13 and on which tissue can grow.

Figure 13:
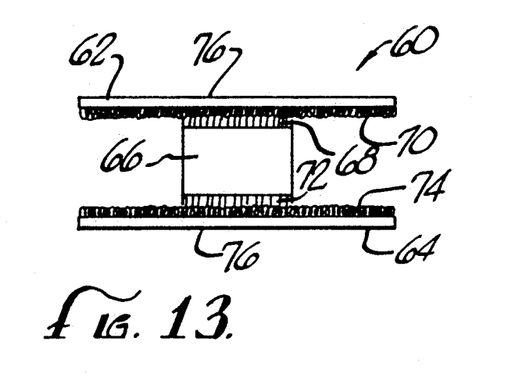
FIG. 13 is a side view of a surgical implantation device such as any of those shown in FIGS. 4–12, with their elements connected by releasable fastening means.

The surgical implantation device in accordance with the invention can be constructed from separate elements that are individually placed in the proper locations and are then attached together to form a single implant structure. FIG. 13 is a cross-sectional view of a surgical implantation device 60 constructed in accordance with the present invention. The implantation device 60 includes a first planar portion 62, a second planar portion 64, and a locating member 66 that extends between the first planar member and the second planar member. The locating member 66 is connected to each of the planar members by a hook-and-loop fastening mechanism, such as that sold under the name of "VELCRO." Thus, one end of the locating member is provided with a first part of a hook-and-loop fastening mechanism 68, and the first planar member 62 is provided with a matching second part of a hook-and-loop fastening mechanism 70 that engages with the first hook-and-loop mechanism 68. Likewise, the opposite end of the locating member 66 is provided with a hook-and-loop fastening mechanism 72 while the corresponding location on the second planar member 64 is provided with a complementary hook-and-loop fastening arrangement 74.

In addition to assembling the surgical implantation device at the hernia site in the patient, the surgical implantation device can also include further refinements that make its use more advantageous. For example, the outwardly facing surfaces of the surgical implantation device 60 shown in FIG. 13 are provided with a smooth coating 76 such as a thin coating of "GORE-TEX", which discourages the formation of scar tissue and prevents the intestine from clinging to the implantation device before tissue has had a chance to grow over it.

Figure 14:
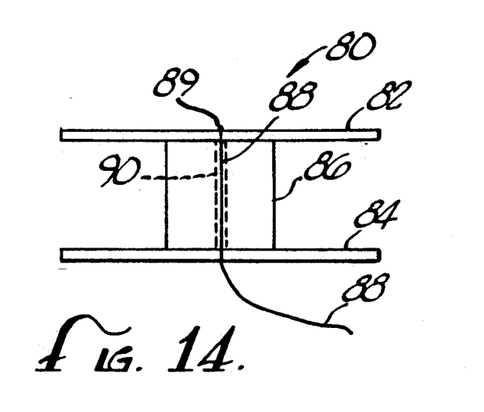
FIG. 14 is a side view of another surgical implantation device constructed in accordance with the present invention with its elements connected by a suture.

FIG. 14 shows yet another surgical implantation device 80 comprised of separate members. The first and second planar patches 82, 84 and the locating member 86 are shown attached together by a suture 88 that can then be tied off at the hernia site. This securely attaches the separate parts together, effectively immobilizing the surgical implantation device at the desired location. The suture is attached to the first planar patch 82 at an attachment point 89 and passes through a central bore 90 in the locating member and passes through the planar patches. The attachment of the separate members together in this way can, under many circumstances, be much easier than assembling the separate elements together using "VELCRO" fasteners or similar attachment mechanisms. Alternatively, the suture 88 can be used in addition to some other attachment mechanism, in which case the suture can be attached to the first planar patch member 82.

After the suture 88 has been attached to the first planar member 82, the first member is deployed. This anchors the suture relative to the fascia opening 13 (FIG. 2). The locating member 86 can then be slipped onto the suture and can then slide down the suture to its proper position at the fascia opening 13. The last planar patch member 84 can then be slipped onto the suture and can then slide down the suture to its proper position. The various members can be attached together by tying off the suture at the last planar member, by means of "VELCRO", or by other means known to those skilled in the art. As discussed, one or both of the planar members 82 and 84 can comprise spoked segments (see FIG. 12).

Figures 15, 16:
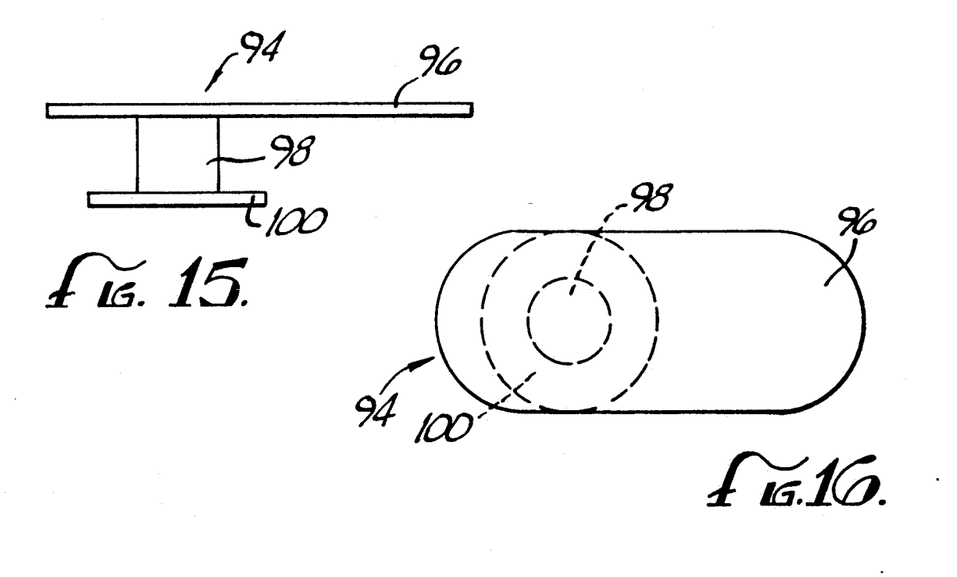
FIG. 15 is a side view of another surgical implantation device in accordance with the present invention with an offset planar patch member.
FIG. 16 is a top plan view of the FIG. 15 surgical implantation device.

FIG. 15 is a side view of another embodiment of a surgical implantation device 94 in accordance with the present invention in which the first planar patch member 96 is offset when compared with the locating plug member 98 and the second planar patch member 100. The offset construction is most effective in the case of a lateral hernia condition, in which the hernia is not close to the patient's midline. In such a case, the first planar patch member 96 can reinforce the abdomen toward the body center. For example, if the hernia is located laterally toward the patient's left, the center of the plug member 98 will be attached to the first planar patch 96 toward the left of the patch's center so that the first patch extends to the right more toward the patient's body center than toward the left side, as shown in FIG. 15. In such a case, the first patch 96 also could have a non-circular, oval shape, as shown in FIG. 16, for greater abdominal reinforcement. The second planar patch member 100 would not have such a critical need to reinforce the abdomen center, and therefore would preferably have a circular shape. Again, the planar members 96 and 100 can comprise fabric patches such as illustrated in FIGS. 9-11 or can comprise spoked segments such as illustrated in FIG. 12.

Those skilled in the art will recognize that variations and combinations of the described members might have particular advantages. For example, in the case of the embodiment of FIG. 3, the maximum pressing force from the patient's internal organs to keep the device in place will occur if the peritoneum is first pierced and then sealed after deployment of the implantation device, rather than if the peritoneum is left intact. In the case of the three-member embodiments of FIG. 4 and FIG. 5, the implantation device can be provided with a first planar member that is spoked (see FIG. 12) and a second planar member that includes a fabric patch (FIGS. 9-11). This decreases the amount of materials used and makes insertion down the surgical tube easier. Other variations will occur to those skilled in the art.

The present invention has been described above in terms of presently preferred embodiments so that an understanding of the present invention can be conveyed. There are, however, many configurations for surgical implantation devices not specifically described herein, but with which the present invention is applicable. The present invention should therefore not be seen as limited to the particular embodiments described herein, but rather, it should be understood that the present invention has applicability with respect to surgical implantation devices in a variety of applications. All modifications, variations, or equivalent arrangements that are within the scope of the attached claims should therefore be considered to be within the scope of the invention.

I claim:

1. A surgical implantation device adapted to be placed within a patient using a surgical tube inserted through the patient's skin, for sealing a wall opening in one of the patient's body cavities, the surgical implant comprising:

a first planar patch member, for bridging the wall opening, that can be compressed into an implanting condition such that it fits within a surgical tube and that can be expanded into a deployed condition upon release from the surgical tube such that it assumes a planar shape;

a second planar patch member, for bridging the wall opening, that can be compressed into an implanting condition such that it fits within a surgical tube and that can be expanded into a deployed condition upon release from the surgical tube such that it assumes a planar shape;

a second planar patch member, for bridging the wall opening, that can be compressed into an implanting condition such that it fits within the surgical tube and that can be expanded into a deployed condition upon release from the surgical tube such that it assumes a planar shape; and a locating member having a predetermined length;

wherein one end of the locating member and one surface of the first patch member include hook and loop fasteners, for removably attaching the two members together, and the opposite end of the locating member and one surface of the second patch member include hook and loop fasteners, for removably attaching the two members together;

wherein the first planar member, locating member, and second planar member are apart in the implanting condition;

and wherein in the deployed condition, the first patch member is positioned on one side of the wall opening in the patient's body cavity, the second patch member is positioned on the other side of the wall opening, and the locating member extends through the wall opening to interconnect the first and second patch members.

2. A surgical implantation device as defined in claim 1, wherein at least one of the patching means includes a biocompatible fabric and resilient means for being folded upon itself and held under compression when in the implanting condition and for automatically assuming the deployed condition when released from compression.

3. A surgical implantation device as defined in claim 2, wherein the resilient means comprises a plurality of resilient strips attached to the biocompatible fabric in radial segments.

4. A surgical implantation device as defined in claim 2, wherein the resilient means comprises a plurality of resilient strips attached to the biocompatible fabric in concentric strips.

5. A surgical implantation device as defined in claim 2, wherein the resilient means comprises a resilient strip attached to the periphery of the biocompatible fabric.

6. A surgical implantation device as defined in claim 5, wherein the resilient means comprises a coiled steel spring.

7. A surgical implantation device as defined in claim 2, wherein at least one of the patching means comprises a plurality of radial segments.

8. A surgical implantation device that can be placed within a patient using a surgical tube inserted through the patient's skin and that, once placed, can be used to seal an enlarged generally circular opening in the wall of one of the patient's body cavities, the surgical implant comprising:

a first flat, circular patch that is constructed of a biocompatible fabric and that includes a plurality of resilient members sufficiently stiff to urge the first patch into a planar orientation and resist any other orientations, but sufficiently flexible to allow the first patch to be folded into a surgical tube;

a second flat, circular patch that is constructed of a biocompatible fabric and that includes a plurality of resilient members sufficiently stiff to urge the second patch into a planar orientation and resist any other orientations but sufficiently flexible to allow the second patch to be folded into the surgical tube; and an elongated locating member that is constructed of a biocompatible material and that includes at a first end hook and loop fastener means, for attaching the member to the first patch, and further includes at a second end hook and loop fastener means, for attaching the member to the second patch, the locating member having a generally cylindrical shape with a diameter substantially the same as the diameter of the circular opening in the wall of the patient's body cavity.

9. A surgical implantation device as defined in claim 8, wherein the resilient members comprise straight segments that are attached to the first and second patches to radiate outwardly from the patch centers.

10. A surgical implantation device as defined in claim 8, wherein the resilient members comprise circular segments that are attached to the first and second patches concentrically about the patch centers.

11. A surgical implantation device as defined in claim 8, wherein the resilient members comprise segments that are woven into the fabric material.

12. A surgical implantation device as defined in claim 8, wherein the elongated locating member includes a plurality of resilient members sufficiently stiff to urge the locating member into a cylindrical orientation when the locating member is not acted upon by external forces, but sufficiently flexible to allow the locating member to be folded into the surgical tube.

13. A method of implanting a surgical implantation device, having a generally planar first portion and second portion that are interconnected by a connecting segment, into a patient using a surgical tube to seal an enlarged, generally circular opening in the wall of one of the patient's body cavities, the method comprising the steps of:

providing a surgical implementation device having a generally planar first portion and second portion that are interconnected by a connecting segment;

inserting and locating one end of a surgical tube through a wall opening, in a wall of a body cavity, and adjacent a first side of the wall;

forcing the first portion of the surgical implantation device out of the surgical tube adjacent the first side of the wall and allowing the first portion to automatically assume a planar shape;

forcing the connecting segment of the surgical implantation device out of the surgical tube within the wall opening;

forcing the second planar portion of the surgical implantation device out of the surgical tube adjacent a second side of the wall and allowing the second portion to automatically assume a planar shape;

passing a suture through the first portion, the connecting segment, and the second portion of the surgical implantation device and tying off the suture, to attach together the first portion, connecting segment, and second portion; and withdrawing the surgical tube from the patient.

* * * * *

UNITED STATES PATENT AND TRADEMARK OFFICE
CERTIFICATE OF CORRECTION

PATENT NO. : 5,254,133

DATED : October 19, 1993

INVENTOR(S) : Arnold S. Seid

It is certified that error appears in the above-identified patent and that said Letters Patent is hereby corrected as shown below:

Column 10, delete lines 39-44 (duplicative of lines 45-50).

Signed and Sealed this

Fifth Day of July, 1994

Attest:

BRUCE LEHMAN

Attesting Officer     Commissioner of Patents and Trademarks